(12) United States Patent
Andersen

(10) Patent No.: US 7,250,040 B2
(45) Date of Patent: Jul. 31, 2007

(54) ARRANGEMENT AT A STOMA BAG

(75) Inventor: Svein Jakob Andersen, Randaberg (NO)

(73) Assignee: Bristol-Myers Squibb Company, New York, NY (US)

( * ) Notice: Subject to any disclaimer, the term of this patent is extended or adjusted under 35 U.S.C. 154(b) by 67 days.

(21) Appl. No.: 10/466,028

(22) PCT Filed: Jan. 8, 2002

(86) PCT No.: PCT/NO02/00007

§ 371 (c)(1),
(2), (4) Date: Oct. 27, 2003

(87) PCT Pub. No.: WO02/058603

PCT Pub. Date: Aug. 1, 2002

(65) Prior Publication Data

US 2004/0073179 A1    Apr. 15, 2004

(30) Foreign Application Priority Data

Jan. 10, 2001   (NO) .................................. 20010160

(51) Int. Cl.
*A61F 5/44* (2006.01)
(52) U.S. Cl. .................. 604/343; 604/332; 604/337; 604/338; 604/341; 604/342
(58) Field of Classification Search ........ 604/332–344, 604/349, 345–348, 355, 350–354
See application file for complete search history.

(56) References Cited

U.S. PATENT DOCUMENTS

| | | | | |
|---|---|---|---|---|
| 2,971,510 A | * | 2/1961 | Berger | 604/342 |
| 3,976,076 A | * | 8/1976 | Beach | 604/349 |
| 4,610,676 A | | 9/1986 | Schneider et al. | |
| 5,178,614 A | * | 1/1993 | McDowell et al. | 604/332 |
| 5,501,677 A | | 3/1996 | Jensen | |
| 5,626,570 A | | 5/1997 | Gallo | |
| 5,947,942 A | * | 9/1999 | Galjour | 604/345 |
| 6,050,982 A | * | 4/2000 | Wheeler | 604/332 |
| 2004/0039357 A1 | * | 2/2004 | Andersen | 604/332 |

FOREIGN PATENT DOCUMENTS

| | | |
|---|---|---|
| DE | 19921555 A1 * | 2/2000 |
| EP | 0 197 783 | 10/1986 |
| EP | 0 277 821 | 8/1988 |
| GB | 2 329 838 | 4/1999 |
| SE | 7601395-2 | 3/1981 |
| SE | 450 203 | 6/1987 |

* cited by examiner

*Primary Examiner*—Tatyana Zalukaeva
*Assistant Examiner*—Ginger Chapman
(74) *Attorney, Agent, or Firm*—Stuart E. Krieger

(57) ABSTRACT

An arrangement at a stoma bag of the type used by persons or animals with a colostoma, including a flexible bag (flexi-bag) and a ring fastener/magazine ring, where the ring fastener/magazine ring is designed to be connected to a stoma plate, and where, in its initial position, the entire flexibag is located in or in close proximity to the ring fastener/magazine ring.

10 Claims, 4 Drawing Sheets

ARRANGEMENT AT A STOMA BAG

RELATED APPLICATIONS

This application is a national phase in the United States of the international application PCT/NO02/00007 and claims the benefit of the Norwegian application number 20010160 filed Jan. 10, 2001.

BACKGROUND OF THE INVENTION

1. Field of the Invention

This invention regards a flexible bag for use by persons with a colostoma. The bag is designed to increase in volume as it fills up with stool.

2. Description of the Related Art

A considerable number of people have undergone operations for injuries and illnesses that entail the colon having to be led out through the abdominal wall. This solution means that stool issuing from the colon is collected in a bag carried on the outside of the body.

Several almost identical solutions are available for collection of stool. All the solutions entail a plate, a so-called stoma plate, normally made from non-rigid plastic and equipped with a central opening adapted to the protruding end of the colon, being guided over the colon and glued to the abdominal skin by the colon by means of an adhesive. On the side facing away from the skin, the plate is provided with an annular bead that seals against the plate. The bead profile varies with the various suppliers' products, but in all cases it is designed to form a fastening for a collection bag for stool, a so-called stoma bag.

Stoma bags according to prior art are designed as a bag with an opening near one of its end portions. The opening is formed in a manner such that it may easily and safely be sealingly connected to the bead of the stoma plate. In this connected-up state, the full length of the stoma bag hangs down along the person's abdomen, filling with stool as the stool issues from the colon. The relatively large physical dimensions of the bag cause it to be difficult to hide, especially when using light clothing.

An obvious solution may be to use a flexible bag, and proposals for the design of such bags have been described in the patent literature. German patent DE 19921555 describes a bellows-shaped stoma bag, which in the initial position is compressed like the bellows of an accordion near the stoma plate. Upon being filled, the bellows bag is extended in the outward direction from the stoma plate. A bag according to DE 19921555 requires relatively little space in the initial position, but will project from the person's body already at a relatively low fill-up level, thereby not constituting a discrete solution.

U.S. Pat. No. 5,947,942 describes in main feature a belt containing a stoma bag in a pocket in the belt. With this solution the potential fill volume is limited. Changing out the stoma bag is complicated, and entails a considerable risk of soiling the belt and the person's fingers.

SUMMARY OF THE INVENTION

The object of the invention is to remedy the disadvantages of prior art.

The object is achieved in accordance with the invention by the characteristics stated in the description below and in the appended claims.

In a preferred embodiment, a stoma plate comprising a protruding threaded portion is guided over the end portion of the colon and glued to the abdominal skin in a sealing manner. A flexible stoma bag, hereinafter termed a flexibag, is, from its open end portion, guided all the way in over a magazine ring sealingly connected to a ring fastener, such that the closed end portion of the flexibag is pulled into/up to the magazine ring. The open-end portion of the flexibag is connected to the magazine ring in a manner such that it cannot come loose inadvertently. The ring fastener has a threaded portion that matches the protruding threaded portion of the stoma plate in a complementary fashion. The ring fastener comprising the pulled-up flexibag constitutes a readily replaceable unit.

The flexibag, which in the initial position is pulled fully in over the magazine ring, is designed to be pulled out of the magazine ring as it fills up with stool. At a suitable time for emptying the flexibag, it may be replaced by a new one or emptied and reused. If the flexibag is to be reused, it may be packed up and guided back into the central opening of the feeder ring after the ring fastener has been re-attached to the stoma plate. A strap, one end of which is fixed to the ring fastener, may be strapped over the packed-up stoma bag and attached to the ring fastener by its other end portion, e.g. by means of mating hook and loop patches such as VELCRO. The purpose of the strap is to keep the flexibag in place in the ring fastener. The mating hook and loop patches, e.g. VELCRO, are designed to disengage when stool flows into the flexibag, so as to allow the bag to expand freely.

The flexibag in conjunction with a matching magazine ring is also well suited for use with stoma plates according to prior art. In this case, the ring fastener is not provided with a thread, but with a peripheral bead or alternatively a groove, which may be fastened to the stoma plate via snap-in retention.

BRIEF DESCRIPTION OF THE DRAWINGS

The following describes a non-limiting example of a preferred embodiment illustrated in the appended drawings, in which.

DETAILED DESCRIPTION OF THE PREFERRED EMBODIMENT

Figure 1:
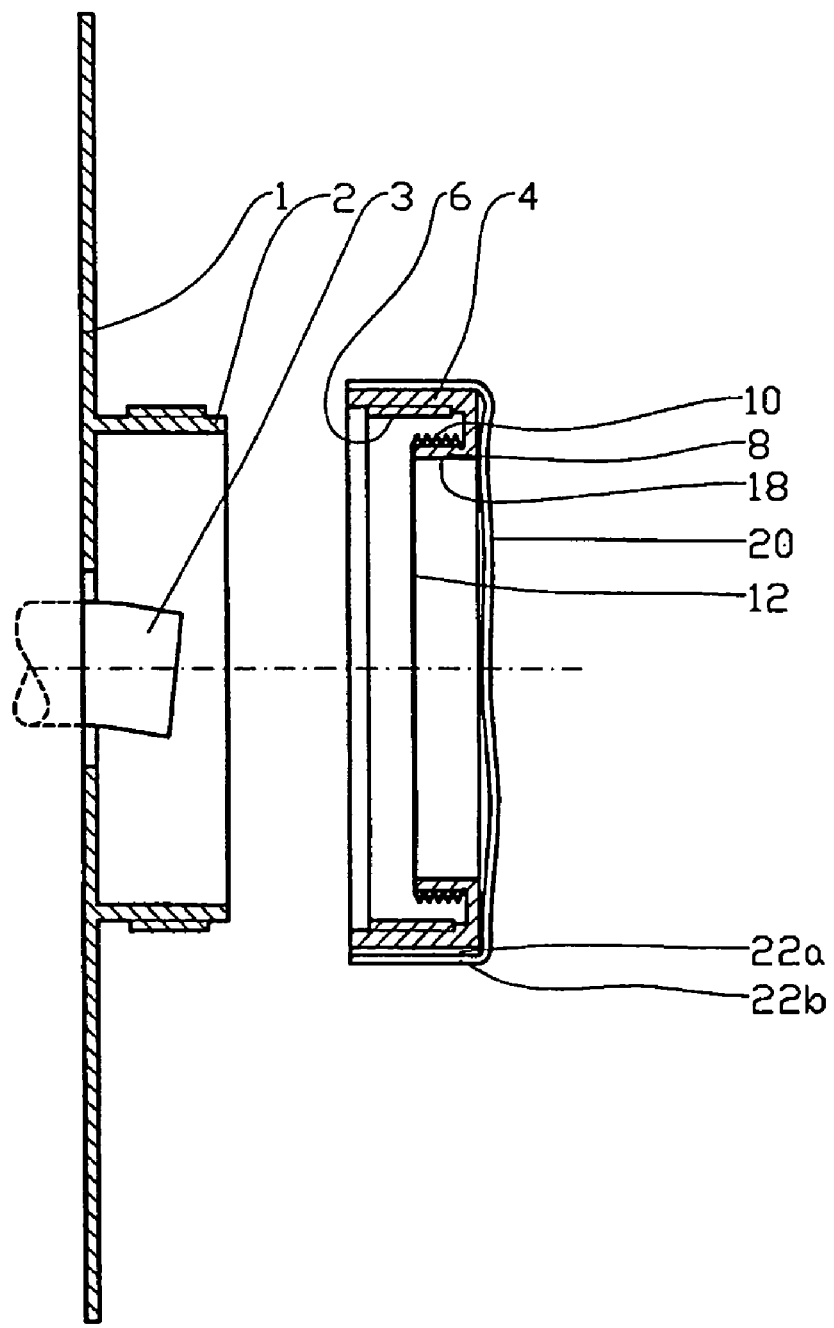
FIG. 1 is a sectional view of a stoma plate and a ring fastener/flexibag prior to coupling.

In the drawings, reference number 1, see FIG. 1, denotes a stoma plate comprising a protruding threaded connecting piece 2. The stoma plate 1 has been guided over a protruding end 3 of the colon (stoma) and glued to the abdominal skin (not shown). A ring fastener 4 comprising a threaded portion 6 and a magazine ring 8 are designed to be releasably connected to the stoma plate 1.

Figure 4:
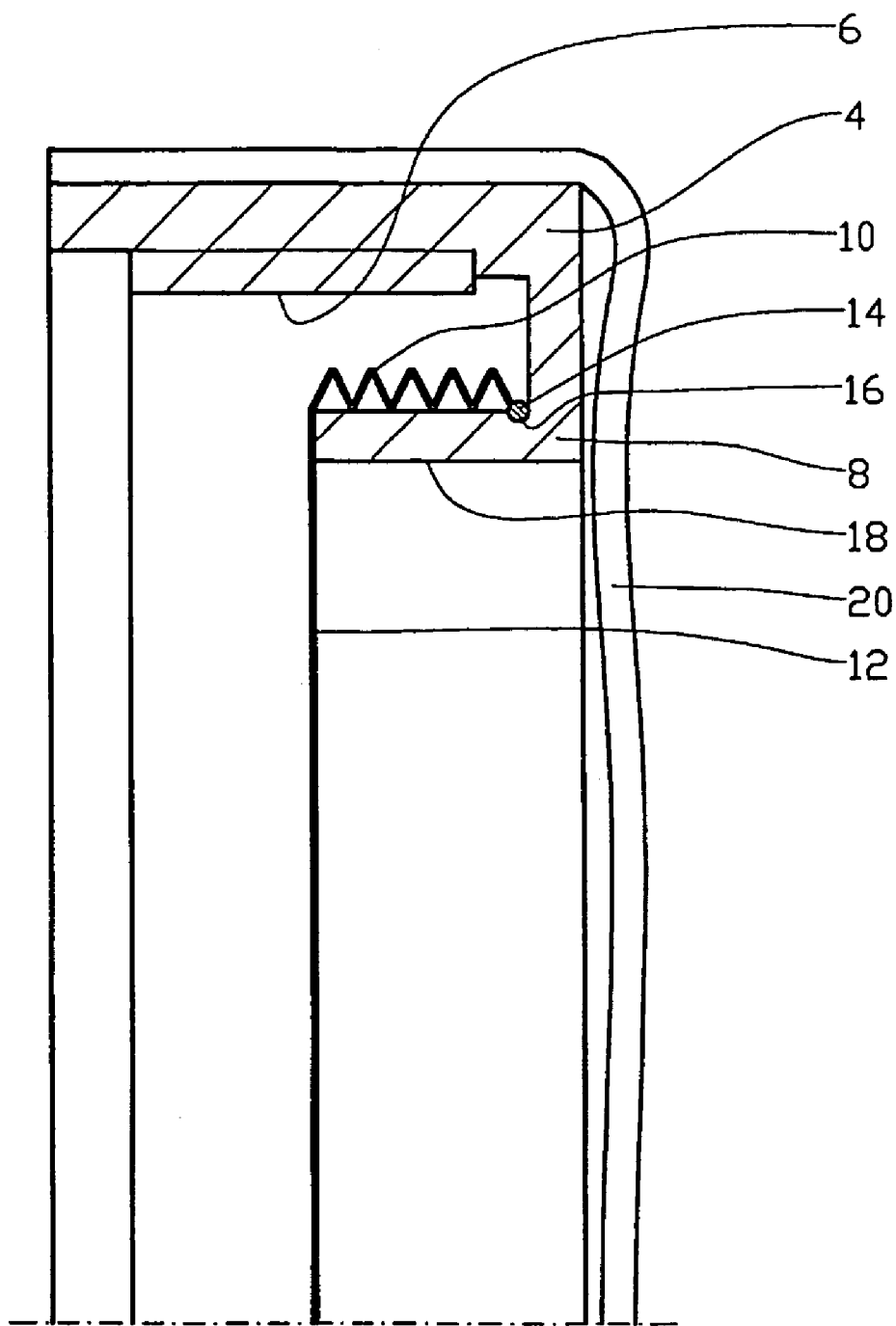
FIG. 4 is an enlarged sectional view of the ring fastener/flexibag of FIG. 1.

A flexibag 10 formed in e.g. a latex material has, from its open end portion, been guided over and pulled up onto the magazine ring 8 in a manner such that only the closed end portion 12 of the flexibag 10 remains outside the magazine ring 8. The open end portion of the flexibag 10 is coupled to the magazine ring, e.g. by a bead 14, which encircles and is sealingly connected to the open end portion of the flexibag 10, being arranged in a circular groove 16 in the magazine ring 8, see FIG. 4. The ring fastener 4 and the flexibag 10 may form one moulding.

Figure 2:
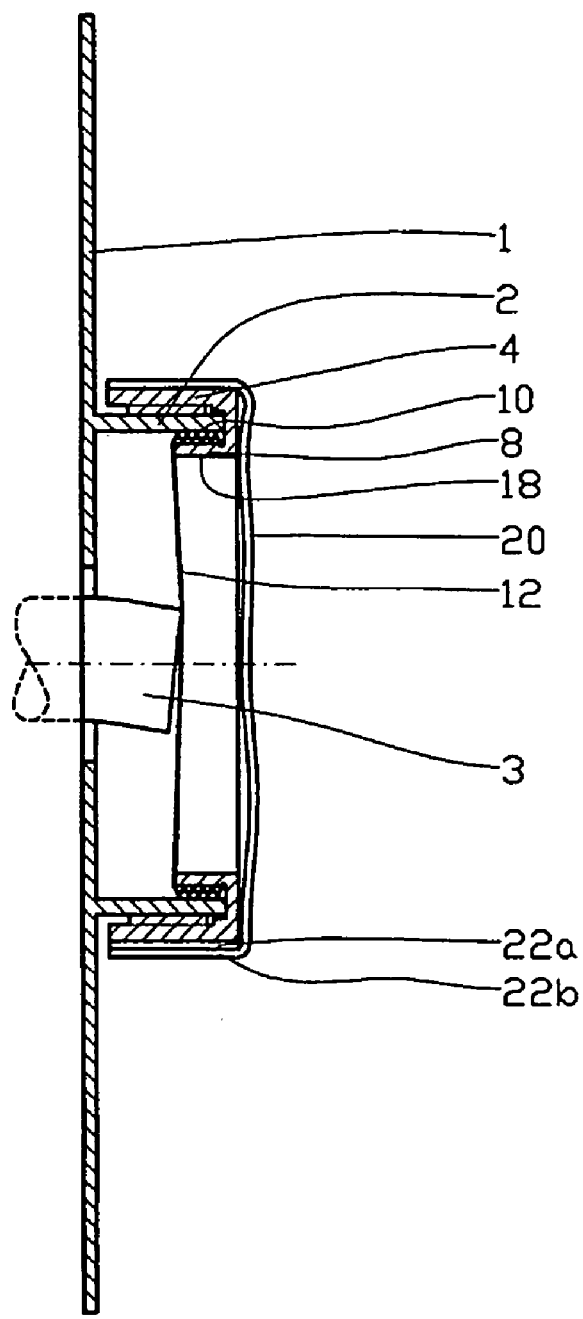
FIG. 2 is a sectional view of a stoma plate and a ring fastener/flexibag after coupling.
Figure 3:
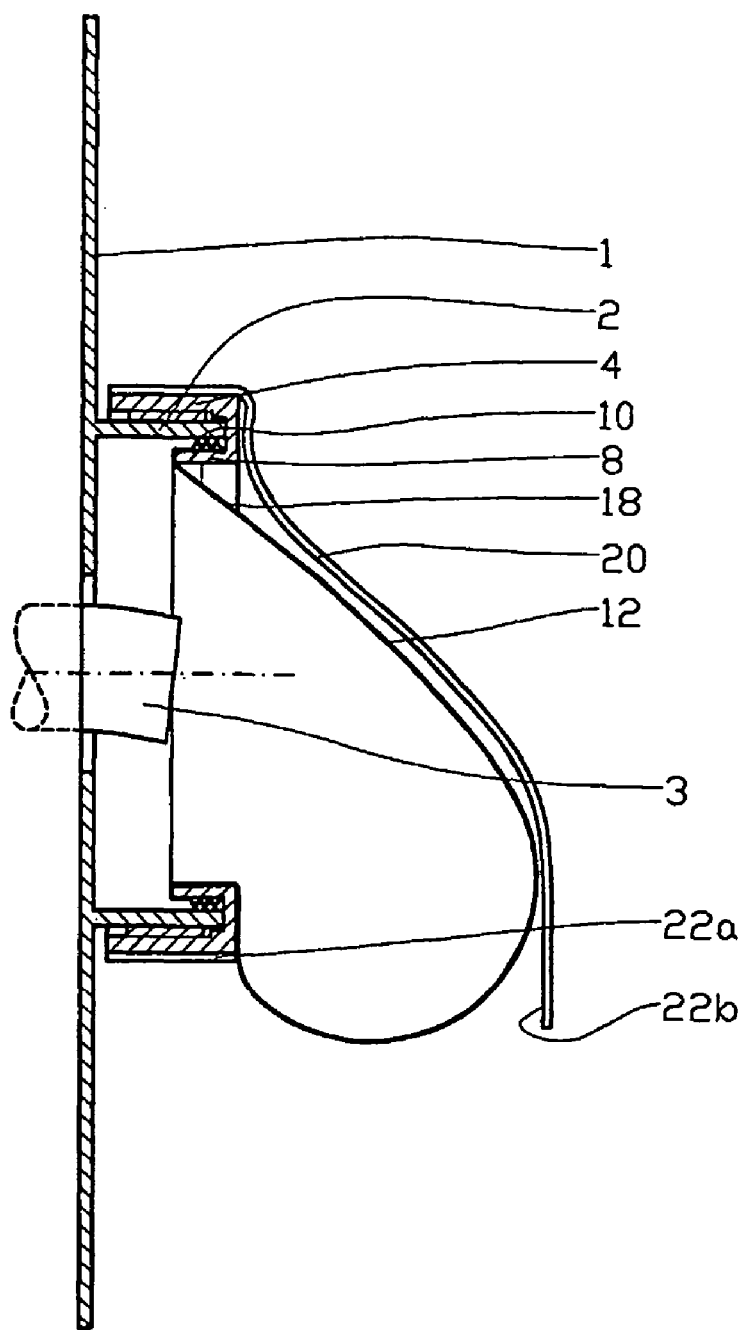
FIG. 3 is a sectional view of a stoma plate and a ring fastener/flexibag, where the flexibag is partially filled.

In a preferred embodiment such as shown in the appended drawings, the ring fastener 4 with an attached flexibag is screwed down onto the protruding portion 2 prior to use, see FIG. 2. In this initial position, the flexibag arrangement 1, 6, 12 requires very little space, and is therefore not very visible. When stool flows in against the flexibag 10, this will stretch, while at the same time being fed out sufficiently from the magazine ring 8, see FIG. 3.

At a suitable time the flexibag 10 with the ring fastener 4 may be replaced with a new one. Or alternatively, the flexibag 10 may be emptied and reused. When the flexibag 10 is to be reused after emptying, part of the flexibag will be outside of the magazine ring 8. This protruding part of the bag may be placed in the central opening 18 of the ring fastener 4. A fastening strap 20, one end of which is fixed to the ring fastener. 4, is designed to be stretched across the opening 18 and be releasably attached to the ring fastener at its other end portion, e.g. by means of Velcro mating hook and loop patches such as VELCRO 22a, 22b. The VELCRO 22a, 22b is formed in a manner such that the felt loop 22a of the VELCRO detaches from the hook 22b of the VELCRO when stool again flows into the flexibag 10, thereby applying pressure on the fastening strap 20.

The cross section of the magazine ring 8 may be cylindrical, conical or have any other expedient geometry. The magazine ring 8 may be round or unround. The abutment surface between the magazine ring 8 and the flexibag 10 has a surface quality that is adapted to the frictional module of the flexibag material in a manner such that the flexibag 10 is pulled out of the magazine ring 8 upon suitable tension in the flexibag. The tension is applied through stool pressing against the wall of the bag 12. A friction controlling material such as talcum may be used between the parts in order to provide the desired friction between the flexibag 10 and the magazine ring 8.

The flexibag 10 may be designed as a double bag, where an internal part constitutes the sealing bag, while an external part is designed as a safety bag which is also designed to be comfortable against the skin.

The use of a flexibag will to a considerable degree reduce the drawbacks for persons who have undergone a colostomy, with regards to both size and visibility of the collection means.

The invention claimed is:

1. A device for a stoma, comprising:
   a. a foldable and unfoldable flexibag having an open end and a closed end for receiving and collecting waste from the stoma;
   b. a stoma plate with an opening adapted for receiving the stoma therein, said stoma plate being attachable to a wearer's skin with the stoma in said opening, said stoma plate also having a protruding portion extending away from the stoma, when said stoma plate is on the wearer's skin; and
   c. attaching means for attaching said flexibag to said protruding portion of said stoma plate, said attaching means including an annular fastening portion for fastening said open end of said flexibag and for releasably capturing substantially the entire length of said flexibag in a folded condition annularly therearound, said attaching means having an aperture aligning with said stoma plate opening, said closed end of said flexibag extending across said aperture so that waste passing from the stoma through said stoma plate opening and aperture of said attaching means contacts said closed end of said flexibag and causes said flexibag to releasably unfold from said fastening portion and collect the waste, said attachment means remaining fixed to said stoma plate when said flexibag unfolds, said attaching means including releasing means extending across said aperture for releasing said closed end of said flexibag to extend through said aperture, said releasing means releasing when said flexibag pushes against it during capture of the waste, wherein said releasing means includes a strap.

2. The device of claim 1 wherein said protruding portion is threaded and said attaching means is secured to said threads.

3. The device of claim 1 wherein said fastening portion is ring shaped and said attaching means includes a complementary coupling for coupling to said protruding portion of said stoma plate.

4. The device of claim 1 wherein said fastening portion is ring-shaped for accommodating said open end of said flexibag therearound and said attaching means further includes a magazine for coupling said attachment means to said protruding portion of said stoma plate.

5. The device of claim 4 wherein said fastening portion and said magazine are an integral piece.

6. The device of claim 1 wherein said flexibag includes a bead and said fastening portion includes a groove configured to accommodate said bead in said groove and releasably fasten said flexibag to said fastening portion.

7. The device of claim 1 wherein said flexibag gradually unfolds from said cavity when waste continues to enter said flexibag.

8. The device of claim 1 further including a safety bag.

9. The device of claim 1 wherein said flexibag may be removed from said fastening portion and replaced by a new or emptied and reused flexibag.

10. The device of claim 1 further comprising a safety bag external to said flexibag.

* * * * *